United States Patent
Tiarks et al.

(10) Patent No.: US 8,142,714 B2
(45) Date of Patent: Mar. 27, 2012

(54) CLEANING AND DISINFECTION OF SURGICAL AND MEDICAL INSTRUMENTS AND APPLIANCES

(75) Inventors: Petra Tiarks, Hamburg (DE); Jürgen Staffeldt, Winsen/Luhe (DE)

(73) Assignee: Chemische Fabrik Dr. Weigert GmbH & Co. KG, Hamburg (DE)

( * ) Notice: Subject to any disclaimer, the term of this patent is extended or adjusted under 35 U.S.C. 154(b) by 1208 days.

(21) Appl. No.: 10/502,925

(22) PCT Filed: Jan. 28, 2003

(86) PCT No.: PCT/EP03/00849
§ 371 (c)(1),
(2), (4) Date: Jul. 28, 2004

(87) PCT Pub. No.: WO03/064580
PCT Pub. Date: Aug. 7, 2003

(65) Prior Publication Data
US 2005/0079097 A1 Apr. 14, 2005

(30) Foreign Application Priority Data
Jan. 28, 2002 (DE) .................. 102 03 225

(51) Int. Cl.
| | |
|---|---|
| C23F 11/06 | (2006.01) |
| A61L 9/00 | (2006.01) |
| A61L 2/00 | (2006.01) |
| C11D 3/00 | (2006.01) |
| C11D 17/00 | (2006.01) |
| A61K 7/50 | (2006.01) |
| A61K 31/74 | (2006.01) |
| G01N 31/00 | (2006.01) |
| C12Q 1/22 | (2006.01) |
| C09K 13/02 | (2006.01) |
| A01N 35/00 | (2006.01) |
| B08B 9/00 | (2006.01) |

(52) U.S. Cl. .................. 422/28; 422/1; 422/13; 422/32; 422/29; 422/292; 422/905; 510/155; 510/331; 510/341; 510/424; 510/413; 510/414; 510/421; 510/422; 510/535; 510/536; 436/1; 436/2; 436/26; 435/31; 435/287.4; 435/236; 435/325; 435/395; 435/177; 435/1.1; 514/693; 134/22.14; 134/22.19; 134/22.13; 134/22.17; 134/29; 424/78.26; 424/665; 424/667; 424/722; 424/70.19; 424/70.21; 424/70.22; 252/79.5

(58) Field of Classification Search ............... 422/1, 13, 422/28, 32, 29, 292, 905; 510/155, 331, 510/341, 424, 413–414, 421–422, 535–536, 510/FOR. 198; 436/1–2, 26; 435/31, 287.4, 435/236, 325, 395, 177, 1.1; 514/693; 134/22.14, 134/22.19, 22.13, 22.17, 29; 424/78.26, 424/665, 667, 722, 70.19, 70.21, 70.22; 252/79.5
See application file for complete search history.

(56) References Cited

U.S. PATENT DOCUMENTS
3,168,478 A * 2/1965 Stefcik et al. ................. 510/436
(Continued)

FOREIGN PATENT DOCUMENTS
CA 2412820 6/2001
(Continued)

OTHER PUBLICATIONS
Levine, David et al. "Cost Awareness and Containment at the Hosptial for Specical Surgery" Clinical Orthopaedics, Feb. 1995.*
(Continued)

*Primary Examiner* — Jill Warden
*Assistant Examiner* — Monzer Chorbaji
(74) *Attorney, Agent, or Firm* — Casmir Jones, S.C.

(57) ABSTRACT

The invention relates to the use of a cleaning agent that contains surfactants and has a pH value of at least 11 when diluted in an aqueous solution and ready for use. Said cleaning agent is used to destabilize prions during mechanical and manual cleaning and/or disinfection of medical and/or surgical instruments and appliances. It has been recognized that this combination enables a reliable destabilization of prions during the mechanical reconditioning of surgical instruments.

18 Claims, 1 Drawing Sheet

U.S. PATENT DOCUMENTS

| | | | | |
|---|---|---|---|---|
| 5,061,395 | A * | 10/1991 | Meng | 510/423 |
| 6,277,805 | B1 * | 8/2001 | Kupneski | 510/384 |
| 6,384,010 | B1 * | 5/2002 | Wagers | 510/470 |
| 6,613,278 | B1 * | 9/2003 | Mills et al. | 422/33 |
| 6,624,132 | B1 * | 9/2003 | Man et al. | 510/392 |
| 6,740,628 | B2 * | 5/2004 | Bennie et al. | 510/221 |
| 6,814,932 | B2 * | 11/2004 | Hlebovy et al. | 422/28 |

FOREIGN PATENT DOCUMENTS

| | | |
|---|---|---|
| DE | 255487 | 6/1976 |
| DE | 19710255 | 9/1998 |
| DE | 10203225 | 7/2003 |
| EP | 0391392 | 4/1990 |
| EP | 0701820 | 3/1996 |
| EP | 0870853 | 10/1998 |
| JP | 07-233396 | 9/1995 |
| JP | 09-020606 | 1/1997 |
| JP | 09-031494 | 2/1997 |
| JP | 11-299867 | 11/1999 |
| JP | 2001-000512 | 1/2001 |
| WO | 98/40107 | 9/1998 |
| WO | 99/18184 | 4/1999 |
| WO | WO01/41896 | 11/2000 |
| WO | 01/62305 | 8/2001 |
| WO | 02/053723 | 7/2002 |

OTHER PUBLICATIONS

Baier, et al. "Activity of an alkaline 'cleaner' in the inactivation of the scrapie agent" Journal of Hospital Infection, vol. 57, pp. 80-84 (2004).

Brown, et al. "Newer Data on the Inactivation of Scrapie Virus or Creutzfeldt-Jakob Disease Virus in Barin Tissue" Journal of Infectious Diseases, vol. 153, pp. 1145-1148 (1986).

Darbord "Inactivation of prions in daily medical practice" (1999) Biomed. & Pharmacother. vol. 53, pp. 34-38.

Henn, et al. "Die Variante der Creutzfeldt-Jakob-Krankheit (vCJK)" Bundesgesundheitsbl, vol. 4, pp. 376-394 (2002).

imeter/MSB, "Oberflachenspannung/CMC: Na-Laurylsulfat (Dodecylsulfat, SDS)" (2006) English Summary Provided.

Haacke, I. "Entwicklungsabschlussbericht," (Nov. 27, 2001) English Summary Provided.

Archives de Documents de la FAO, "L'hygiene dans l'industrie alimentaire Les produits et l'application de l'hygiene," (1993) English Summary Provided.

Prusiner et al., "Thyiocyanate and hydroxyl ions inactivate the scrapie agent," PNAS, 78(7):4606-4610 (1981).

WFHSS, "Annual EFHSS Conference 2001," (2001).

EFHSS, "Success in Small Steps," 2nd EFHSS Congress in Brugge, Belgium, Nov. 5-6, 2001, Conference Report by Gudrun Droop, (2001).

Renel-King, K., "Transcript of part of Dr. Staffeldt's speech of Nov. 6, 2001 at the 2nd EFHSS Congress in Brugge," (2001).

Patent Abastracts of Japan, English Machine Translation of JP Patent Publication 2001-000512, published Jan. 9, 2001, translation retrieved Aug. 30, 2006.

Patent Abastracts of Japan, English Machine Translation of JP Patent Publication 07-233396, published Sep. 5, 1995, translation retrieved Aug. 30, 2006.

Patent Abastracts of Japan, English Machine Translation of JP Patent Publication 09-020606, published Jan. 21, 1997, translation retrieved Aug. 30, 2006.

Patent Abastracts of Japan, English Machine Translation of JP Patent Publication 09-031494, published Fe. 4, 1997, translation retrieved Aug. 30, 2006.

Patent Abastracts of Japan, English Machine Translation of JP Patent Publication 11-299867, published Nov. 2, 1999, translation retrieved Aug. 30, 2006.

SMP GmbH "Performance study of Neodisher V4009/1 and Neodisher V4059/5 against prion on surgical metal surface and in brain homogenates suspension," (2003).

* cited by examiner

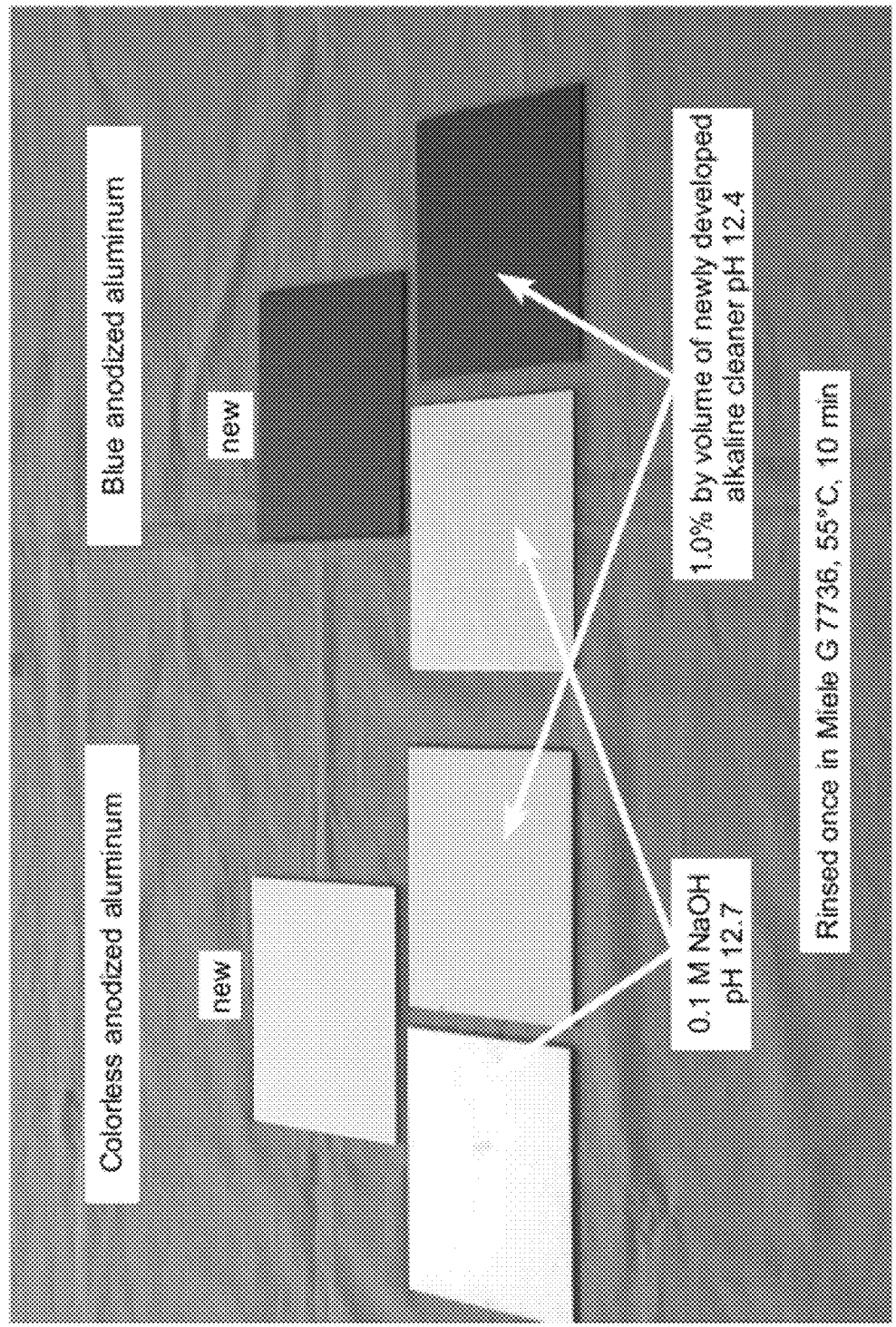

CLEANING AND DISINFECTION OF SURGICAL AND MEDICAL INSTRUMENTS AND APPLIANCES

This application is a §371 US National Entry of International Application No. PCT/EP03/00849 filed Jan. 28, 2003, hereby incorporated herein by reference, which claims priority to German Patent Application Ser. No. 102 03 225.4, filed Jan. 28, 2002.

FIELD OF THE INVENTION

The invention relates to the field of cleaning and disinfection of medical and/or surgical instruments and apparatuses.

BACKGROUND OF THE INVENTION

Creutzfeldt-Jakob Disease (CJD), according to current knowledge, is an encephalopathy caused by prions. Prions are infectious protein particles which cannot be readily destabilized by conventional substances attacking nucleic acid and have high stability toward chemical and physical influences. Cleaning and disinfection of medical or surgical instruments and apparatuses which are possibly contaminated with prions is therefore problematic. In the literature (Bundesgesundheitsblatt July 1998, 279-298), it is proposed to decontaminate instruments contaminated with CJD material using 1 to 2 M NaOH for a period of 24 h, or by steam sterilization for a period of 1 h at 134° C. Alternatively, decontamination using the highly toxic guanidinium thiocyanate is proposed. These decontamination processes are extremely complex and cannot be carried out in the routine preparation of instruments.

SUMMARY OF THE INVENTION

The object underlying the invention is to provide a possible method for the cleaning or disinfection of medical or surgical instruments and apparatuses, in which prions are destabilized with sufficient reliability, preferably are also inactivated. The invention is to be suitable for routine use, in particular in mechanical instrument cleaning and preparation and is not to require any complex separate decontamination, as in the prior art.

The invention therefore relates to the use of a cleaning composition which comprises surfactants and has a pH of at least 11 when diluted in aqueous solution in ready-to-use form, for destabilizing and/or inactivating prions in the mechanical or manual cleaning and/or disinfection of medical and/or surgical instruments and apparatuses.

First some terms used in the context of the invention are to be explained.

DEFINITIONS

The term cleaning composition denotes any ready-to-use formulation which is used either directly or diluted with water for the cleaning or disinfection of the corresponding instruments. In the context of the invention, the term cleaning composition includes the term disinfectant. The cleaning composition can be formulated in solid form or preferably in liquid form. As cleaning solution, that is to say diluted in aqueous solution in ready-to-use form, the cleaning composition has a pH of 11 or above.

The cleaning composition used according to the invention comprises surfactants. This denotes compounds which lower the surface tension, that is to say amphiphilic compounds having at least one hydrophobic moiety and one hydrophilic moiety. In the context of the invention, it is possible to use all surfactants, for example anionic surfactants, nonionic surfactants, cationic surfactants, amphoteric surfactants and block copolymers (in particular made from ethylene oxide and propylene oxide units). By way of example, reference is made to Römpp Chemielexikon [Römpp's Chemistry Lexikon], 10th edition, headword "surfactants".

The invention is used in the mechanical and manual cleaning and/or disinfection of medical and/or surgical instruments and/or apparatuses. "Mechanical" means that the process preferably proceeds automatically in a dishwashing machine and no human intervention is necessary in the course of cleaning or disinfection. In particular, according to the invention, a conventional dishwashing and preparation machine for surgical instruments can be employed. Particularly preferably, the invention is used in mechanical cleaning and disinfection. It can be used, in particular, for routine daily instrument cleaning.

The terms "cleaning and/or disinfection" cover the steps required in the treatment of used instruments and apparatuses up to the preferably sterile state in which they can be reused.

Medical and/or surgical instruments and apparatuses are all appliances used in the medical and hospital sector and parts thereof which are in principle accessible to mechanical cleaning and disinfection.

Destabilizing prions means that infectious prion material possibly adhering to the instrument surface is at least partially destabilized. In a destabilization, the pathogenic conformation of the prion molecule is no longer present.

Prion inactivation has occurred if, in an animal test, it is established that the infectivity of a prion-containing brain extract is no longer present after a treatment with a composition or process under test.

DESCRIPTION OF THE INVENTION

It is known that prions are embedded in fatty tissue and are themselves hydrophobic and are thus accessible with difficulty to water and aqueous solutions.

The invention is based on the surprising finding that prions may be destabilized relatively simply in a strongly alkaline environment, if a surfactant is simultaneously present, in the context of routine, in particular mechanical, instrument cleaning and preparation. The exact mechanism of action of the inventive combination has not been studied, but it is assumed to start from the fact that surfactants loosen the tertiary structure of the prions and thus facilitate their destabilization in the alkaline environment. The pH of the cleaning solution diluted in ready-to-use form is preferably at least 11, further preferably at least 11.5, further preferably at least 12, further preferably at least 12.5. The cleaning composition preferably comprises alkali metal hydroxides such as sodium hydroxide or preferably potassium hydroxide. The use of potassium hydroxide facilitates the provision of a cleaning composition in the form of a concentrate, since potassium hydroxide solutions, at low temperatures, have a lesser tendency to crystallize out than sodium hydroxide solutions. The cleaning composition can additionally comprise alkanolamines.

The addition of surfactants to the highly alkaline cleaning solution can markedly reduce the surface tension and interfacial tension. It is thought that the prions are thereby made more accessible to the alkaline active ingredient and at least the tertiary structure of the prions can be destroyed and the prions can be destabilized or inactivated.

In principle, nonionic surfactants, for example fatty alcohols, are most suitable for reducing the surface tension of an aqueous solution. They have the additional advantage that they foam less and thus prevent or reduce the unwanted foam formation in the cleaning of medical instruments. Foam formation can impair in particular the cleaning of for example narrow-bore tubes of endoscopes or the like. Nonionic surfactants, however, in a strongly alkaline environment, are often difficult to bring into solution. It is therefore preferred in the context of the invention to combine the nonionic surfactant with cationic, anionic or particularly preferably amphoteric surfactants which can act as solubilizer for the nonionic surfactant.

The cleaning solution diluted in ready-to-use form preferably has a surface tension of less than 50 mN/m, preferably less than 40 mN/m, further preferably less than 35 mN/m, further preferably less than 30 mN/m. The surface tension is determined by the plate-ring method as specified in DIN 53993.

A further aspect of the invention is avoiding or reducing the redeposition of prion-containing contaminants on the instruments. The term redeposition denotes the redeposition of a contaminant already removed from a contaminated surface onto another, possibly previously uncontaminated, surface of the instrument to be cleaned. Redeposition is a particular problem with the decontamination, by 24-hour immersion in 1 to 2 M NaOH, recommended in the Bundesgesundheitsblatt (July 1998, 279-298).

The use of surfactants, provided in the context of the invention, already prevents redeposition, since the surfactants can emulsify detached prion constituents and thus keep them in suspension in the aqueous solution. Particularly preferably, in the context of the invention, to avoid or decrease redeposition, the cleaning composition additionally comprises hardness dispersants. Hardness dispersants which can be used are, for example, phosphates and polyphosphates, complexing agents or chelating agents, or other builders. Hardness dispersants support the emulsifying action of the surfactants and thus contribute to the prevention of redeposition.

An important aspect of the invention is its suitability for routine, in particular mechanical, instrument cleaning and preparation. For such routine cleaning, in the prior art, customarily weakly acidic or weakly alkaline (for example enzymatic) cleaners are used, since strongly alkaline solutions can lead to increased loading or corrosion and thus wear of various materials and surfaces which are used in medical instruments and apparatuses. Problems from this point of view are, for example, silicone elastomers, chrome-plated instruments, soldered compounds of silver and tin, adhesive bonds and sealing materials, plastic coatings, for example color codings, glass fiber light conductors and optical surfaces having an antireflection coating. Particular problems are aluminum surfaces, in particular anodized aluminum surfaces, since alkaline solutions exhibit particular aggression toward these. Said problems occur, for example, particularly in the cleaning of endoscopes and constituents thereof, since here the surfaces to be cleaned have a great variety of materials.

In a particularly preferred embodiment of the invention, the cleaning composition therefore additionally comprises corrosion inhibitors. This covers any substance which, in the alkaline solution, inhibits its attack on surfaces, in particular having metallic surfaces such as aluminum or anodized aluminum. Suitable inhibitors are, for example, polymeric silicates, for example waterglass, phosphoric acid esters, or the like. Suitable phosphoric acid esters are mono- and/or diesters of phosphoric acid with aliphatic alcohols of chain length $C_1$ to $C_{22}$ and/or aliphatic diols and/or aliphatic polyols of chain length $C_2$ to $C_{22}$. Particular preference is given to a diester of phosphoric acid with butanol on one side and ethylene glycol on the other. This ester is commercially available under the name Hordaphos® MDGB. According to the invention, despite the use of highly alkaline cleaning solutions, a mild action on, for example, anodized aluminum surfaces is achieved in this manner.

According to the invention, from the constituents of the cleaning composition, preferably a liquid concentrate is formulated which can be diluted with water to give the ready-to-use cleaning solution. In this concentrate, the alkali content (calculated as KOH) is preferably between 2 and 30% by weight, further preferably 35% by weight, further preferably 10 and 30% by weight, further preferably 15 and 25% by weight. The surfactant content is preferably between 2 and 25% by weight, further preferably 2 and 15% by weight, further preferably 5 and 15% by weight, further preferably 5 and 10% by weight. This concentrate is preferably made up at concentrations of 0.5 to 5, preferably 0.5 to 2, particularly preferably 0.5 to 1.5, percent by volume with water to give a ready-to-use solution.

As mentioned above, the concentrate can comprise at least one complexing agent, in particular chelating agent. The complexing agents serve to soften water and can enhance the cleaning action compared with lime soaps by complexing alkaline earth metal ions. The complexing agents can be homo-, co- or terpolymers based on acrylic acid or alkali metal salts thereof, in addition phosphonic acids or alkali metal salts thereof, for example 1-hydroxyethane-1,1-diphosphonic acid, aminotrismethylenephosphonic acid, ethylenediaminotetrakismethylenephosphonic acid, phosphonobutanetricarboxylic acid, tartaric acid, citric acid and gluconic acid; in addition nitrilotriacetic acid or ethylenediaminetetraacetic acid or salts thereof.

The concentrate can comprise nitrilotriacetic acid and/or a salt of this acid, particularly preferably its trisodium salt. The addition of NTA is advantageous if the concentrate is to be made up with water having high mineral contents (hard water) to give a ready-to-use solution.

To the concentrate, there can be added customary preservatives, for example p-hydroxybenzoic acid or methyl esters thereof, 5-bromo-5-nitro-1,3-dioxane, salicylic acid, 2-naphthyl-m-N-dimethylthiocarbanilate, 5-chloro-5-methyl-4-isothiazolin-3-one, 2-methyl-4-isothiazolin-3-one and also mixtures of the two last-mentioned compounds. A preferred preservative is p-hydroxybenzoic acid or methyl esters thereof. Using these preservatives avoids microbial and fungal infestation of the cleaning composition concentrate.

If required, formulation aids (solubilizers) can be added, for example sodium cumenesulfonate, sodium toluene-sulfonate, sodium xylenesulfonate, urea, glycols, in particular polypropylene glycols and polyethylene glycols, methylacetamide and fatty alcohols, for example cetyl alcohol.

The enumeration of possible constituents is not limiting. In addition, it is possible to add, for example, wetting agents, emulsifiers, antifoam agents or the like. It is advantageous, for example, to add N-acyl glutamate as wetting agent.

The time of action of the cleaning composition is according to the invention preferably 1 to 60 min, further preferably 1 to 30 min, further preferably 5 to 30 min, further preferably 10 to 20 min. Before and/or after the action of the inventively used cleaning composition, further preliminary cleaning, cleaning, rinsing or final rinsing or disinfection steps can be provided. It is preferred first to carry out a preliminary rinse to remove coarse contaminants, then to perform an inventive cleaning/disinfection, followed by a rinse with hot water (93° C.) for thermal disinfection and removal of cleaning composition residues.

The cleaning is carried out according to the invention, preferably at a temperature from room temperature to 93° C., further preferably from 40 to 93° C., further preferably from 50 to 80° C., particularly preferably from 50 to 60° C. Likewise preference is given to a temperature range from room temperature (18° C.) to 50° C. or from room temperature to 40° C.

In the case of mechanical cleaning, particular preference is given to temperatures from 50 to 60° C., in particular about 50° C., and a time of action of 10 to 20 min, preferably about 10 min. In the case of manual cleaning by immersion in a cleaning solution, preference is given to a time of action of about 10 min at room temperature. In the case of manual cleaning, preferably a higher concentration, preferably a concentration of the cleaner which is twice as high as in the mechanical cleaning, is used. For example, the cleaner concentrate according to the example 1 below is used in the context of mechanical cleaning preferably in a use concentration of about 0.5% by volume, in manual cleaning at a concentration of 1% by volume.

Illustrative examples of the invention are described hereinafter on the basis of the illustration and the examples.

DESCRIPTION OF THE DRAWINGS

The illustration shows anodized aluminum plates before and after treatment with two different highly alkaline cleaners.

EXPERIMENTAL EXAMPLES

Example 1

A cleaning composition concentrate is prepared according to the table below. The amounts of the starting materials to be used are given in parts by weight.

| | |
|---|---|
| Potassium tripolyphosphate, 50% | 42.78 |
| Potassium hydroxide, 45% | 22.32 |
| Sodium alkylaminodipropionate | 6.00 |
| Bardac LF[1] | 0.50 |
| Fatty alcohol, C10/12, 4EO, 4–5 PO[2] | 0.50 |
| Sodium waterglass | 27.90 |

[1]Cationic surfactant (dioctyldimethylammonium chloride)
[2]Block copolymer of C10/C12 fatty alcohols having 4 ethylene oxide units and 4–5 propylene oxide units.

Example 2

In a one-tank washing machine for medical and surgical instruments, the instruments which are to be cleaned and which are suspected to have a contamination with prions are first pre-rinsed with cold water. The washing machine is then filled with cold water and the cleaning composition concentrate according to example 1 is added at a concentration of 0.5% by volume. The cleaning solution is heated to 55° C. and circulated for 10 min at this temperature with spraying of the instruments. Rinsing is then performed with cold deionized water. Finally a thermal disinfection with deionized water is performed at 93° C. This thermal disinfection is simultaneously the final rinse.

Example 3

The surface tension was determined as specified in DIN 53993 for the following liquids:

| | |
|---|---|
| dionized water | 73 mN/m |
| 0.1 N NaOH in deionized water | 72 mN/m |
| 1% by volume cleaner solution according to example 1 in Hamburg city water | 33 mN/m |

It is seen that the cleaning solution from a concentrate according to example 1 has a markedly decreased surface tension compared with a simply alkaline solution. This solution comprises the fatty alcohol as nonionic surfactant and also sodium alkylaminodipropionate as solubilizing amphoteric surfactant.

Example 4

Roughened microscope slides are dirtied with 50 mg of a blood-egg yolk mixture, dried at 55° C. for 2 h and then immersed in a stirred bath for 10 min at room temperature. The medium used for the immersion bath is deionized water, 0.1 N NaOH or a 1% strength by volume cleaning solution of the cleaning composition concentrate according to example 1. The residual amount of fouling then determined is 20% by weight for water, 35% by weight for 0.1 N NaOH and less than 5% by weight for the cleaner, as immersion bath medium used.

Example 5

To test the care of material of anodized aluminum surfaces, anodized aluminum plates are exposed to a cleaning medium in the Miele G7736 dishwashing machine for 10 min at 55° C. Both new colorless and also blue anodized aluminum plates are used. The cleaning medium is 0.1 M NaOH having a pH of 12.7 and a 1% strength by volume cleaning solution of the cleaning composition concentrate according to example 1. The plates are then inspected visually. The results shown in the illustration shows that in the plates treated with NaOH, the anodized layer is markedly eroded. In contrast thereto, the plates treated with the cleaner have no visible damage to the anodized layer.

The invention claimed is:

1. A method of routine cleaning of and prion destabilization on reusable medical and/or surgical instruments and apparatuses after use and prior to reuse, comprising:
   a) providing:
      i) a surface of a reusable medical or surgical instrument or apparatus contaminated with a prion; and
      ii) a composition comprising surfactants and KOH, wherein said composition has a pH of at least 11.5 when diluted in an aqueous solution in ready-to-use form, for destabilizing prions in the routine mechanical or manual cleaning and/or disinfection of said reusable medical or surgical instrument or apparatus prior to reuse; and
   b) treating said surface of said reusable medical or surgical instrument or apparatus with said composition, wherein the time of action of the cleaning composition is 5 to 30 min, wherein said treatment causes the destabilization of prions on said surface of said reusable medical or surgical instrument or apparatus, and wherein said treating has less corrosive effect on the material of said surface than treatment of the material of said surface with NaOH at a concentration of 1 N or greater.

2. The method of claim 1, wherein said composition has a pH of at least 12.

3. The method of claim 2, wherein said composition has a pH of at least 12.5.

4. The method of claim 1, wherein said composition further comprises alkanolamines.

5. The method of claim 1, wherein said surfactants comprise nonionic surfactants.

6. The method of claim 1, wherein said composition has a surface tension of less than 50 mN/m.

7. The method of claim 1, wherein said composition has a surface tension of less than 40 mN/m.

8. The method of claim 1, wherein said composition has a surface tension of less than 35 mN/m.

9. The method of claim 1, wherein said composition has a surface tension of less than 30 mN/m.

10. The method of claim 1, wherein said composition comprises hardness dispersants.

11. The method of claim 1, wherein said composition comprises one or more of phosphates or polyphosphates.

12. The method of claim 1, wherein said composition comprises one or more corrosion inhibitors.

13. The method of claim 12, wherein said one or more corrosion inhibitors are selected from the group consisting of polymeric silicates and phosphoric acid esters.

14. The method of claim 1, wherein said treating is for a time period of 10 to 20 minutes.

15. The method of claim 1, wherein said treating is performed at temperature from room temperature to 93° C.

16. The method of claim 1, wherein said treating is performed at temperature of from room temperature to 93° C.

17. The method of claim 1, wherein said treating is performed at temperature of from 40 to 93° C.

18. The method of claim 1, wherein said treating is performed at temperature of from 50 to 60° C.

* * * * *